United States Patent
Ahn et al.

(10) Patent No.: US 10,613,032 B2
(45) Date of Patent: Apr. 7, 2020

(54) SPECTROSCOPY APPARATUS, SPECTROSCOPY METHOD, AND BIO-SIGNAL MEASURING APPARATUS

(71) Applicant: SAMSUNG ELECTRONICS CO., LTD., Suwon-si (KR)

(72) Inventors: Sung Mo Ahn, Yongin-si (KR); Seok Ho Yun, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/196,450

(22) Filed: Nov. 20, 2018

(65) Prior Publication Data

US 2019/0154584 A1   May 23, 2019

(30) Foreign Application Priority Data

Nov. 21, 2017   (KR) .................. 10-2017-0155911

(51) Int. Cl.

| | | |
|---|---|---|
| *G01N 21/65* | (2006.01) | |
| *G01N 33/49* | (2006.01) | |
| *G01J 3/02* | (2006.01) | |
| *G01J 3/18* | (2006.01) | |
| *G01J 3/26* | (2006.01) | |

(Continued)

(52) U.S. Cl.
CPC ............ *G01N 21/65* (2013.01); *G01J 3/0208* (2013.01); *G01J 3/0216* (2013.01); *G01J 3/14* (2013.01); *G01J 3/18* (2013.01); *G01J 3/26* (2013.01); *G01N 33/49* (2013.01); *G01J 2003/1213* (2013.01)

(58) Field of Classification Search
CPC .......... G01J 3/4412; G01J 3/44; G01J 3/0272; G01J 3/18; G01J 3/14; G01J 2003/4424; G01N 21/65; G01N 33/49
See application file for complete search history.

(56) References Cited

U.S. PATENT DOCUMENTS

| | | | |
|---|---|---|---|
| 5,351,121 A * | 9/1994 | Baer .................... | G01J 3/44 356/301 |
| 5,886,784 A | 3/1999 | Engelhardt | |

(Continued)

FOREIGN PATENT DOCUMENTS

| | | |
|---|---|---|
| CN | 106645093 A | 5/2017 |
| EP | 2 426 470 A1 | 3/2012 |

(Continued)

OTHER PUBLICATIONS

Kevin K. Tsia, "Performance of serial time-encoded amplified microscope", 2010 Optical Society of America (Year: 2010).*

(Continued)

*Primary Examiner* — Maurice C Smith
(74) *Attorney, Agent, or Firm* — Sughrue Mion, PLLC

(57) ABSTRACT

A spectroscopy apparatus, a spectroscopy method, and a bio-signal measuring apparatus are provided. The spectroscopy apparatus may include: a dispersive element configured to divide an incident light into a plurality of lights having different output angles; and a filter array configured to divide the plurality of lights, with a higher spectral resolution than a spectral resolution of the dispersive element, and provide the divided plurality of lights to a detector.

23 Claims, 18 Drawing Sheets

(51) Int. Cl.
*G01J 3/14* (2006.01)
*G01J 3/12* (2006.01)

(56) References Cited

U.S. PATENT DOCUMENTS

| | | | | |
|---|---|---|---|---|
| 6,052,536 | A * | 4/2000 | Arai | G03B 7/09908 396/100 |
| 7,262,918 | B1 * | 8/2007 | Yoo | H01S 3/005 359/618 |
| 7,944,557 | B2 * | 5/2011 | Hagler | G01J 3/02 356/310 |
| 2004/0104346 | A1 | 6/2004 | Devitt et al. | |
| 2006/0077383 | A1 | 4/2006 | Knebel et al. | |
| 2007/0103679 | A1 | 5/2007 | Yoo | |
| 2009/0040516 | A1 * | 2/2009 | Fritz | G01J 3/02 356/301 |
| 2012/0038919 | A1 | 2/2012 | Ikeda | |
| 2012/0140214 | A1 | 6/2012 | Shibayama et al. | |
| 2013/0215404 | A1 | 8/2013 | Den Boef | |
| 2013/0329225 | A1 | 12/2013 | Shibayama et al. | |
| 2015/0043001 | A1 | 2/2015 | Ishimaru | |
| 2015/0177429 | A1 | 6/2015 | Darty | |
| 2016/0116399 | A1 | 4/2016 | Hruska et al. | |
| 2016/0177366 | A1 * | 6/2016 | Auner | G01J 3/44 |
| 2016/0290863 | A1 | 10/2016 | Goldring et al. | |
| 2017/0176251 | A1 * | 6/2017 | Yokino | G01J 3/0291 |
| 2018/0275064 | A1 | 9/2018 | Li et al. | |
| 2019/0025122 | A1 | 1/2019 | Nayak et al. | |
| 2019/0101444 | A1 * | 4/2019 | Yoon | G01J 3/0256 |

FOREIGN PATENT DOCUMENTS

| | | |
|---|---|---|
| KR | 10-2009-0034245 A | 4/2009 |
| KR | 10-1078135 B1 | 10/2011 |
| KR | 10-1526870 B1 | 6/2015 |
| KR | 10-2017-0087321 A | 7/2017 |
| WO | 2017/180128 A1 | 10/2017 |

OTHER PUBLICATIONS

Christopher M. Limbach, "Development of a Virtually Imaged Phase Array (VIPA) Spectrometer for Diagnostic Applications", Jun. 2018 (Year: 2018).*

Kazunori Tanaka et al., "Compound parabolic concentrator probe for efficient light collection in spectroscopy of biological tissue", Applied Optics, vol. 35, No. 4, Optical Society of America, Washington, DC, XP000577616, Feb. 1, 1996, pp. 758-763.

Communication dated May 7, 2019, issued by the European Patent Office in counterpart European Application No. 18207531.7.

* cited by examiner

SPECTROSCOPY APPARATUS, SPECTROSCOPY METHOD, AND BIO-SIGNAL MEASURING APPARATUS

CROSS-REFERENCE TO RELATED APPLICATION(S)

This application claims priority from Korean Patent Application No. 10-2017-0155911, filed on Nov. 21, 2017, in the Korean Intellectual Property Office, the disclosure of which herein is incorporated by reference in its entirety.

BACKGROUND

1. Field

Apparatuses and methods consistent with exemplary embodiments relate to spectroscopy technology for measuring a spectrum emitted or absorbed by materials.

2. Description of the Related Art

A spectrometer is used for qualitative analysis, quantitative analysis, state analysis of materials by measuring a spectrum emitted from or absorbed into the materials. Such spectrometer may measure a bio-signal related to blood glucose, cholesterol, and the like in a non-invasive manner from a living body. When the spectrometer is mounted in a wearable device, a mobile device, and the like, the spectrometer may be used in the mobile healthcare field as the spectrometer may measure various bio-signals in the non-invasive manner. To this end, the spectrometer may need to be manufactured in a small size.

SUMMARY

One or more exemplary embodiments provide are a spectroscopy apparatus and a spectroscopy method, and a bio-signal measuring apparatus, which may increase spectral resolution while realizing a small size.

According to an aspect of an exemplary embodiment, there is provided a spectroscopy apparatus, including: a dispersive element configured to divide an incident light into a plurality of lights having different output angles; and a filter array configured to divide the plurality of lights, with a higher spectral resolution than a spectral resolution of the dispersive element, and provide the divided plurality of lights to a detector.

The spectroscopy apparatus may further include a collimating lens configured to collimate and transfer the incident light to the dispersive element.

The dispersive element may include a transmissive diffraction grating configured to divide the incident light into the plurality of lights having the different output angles.

The dispersive element may include a prism configured to divide the incident light into the plurality of lights having the different output angles.

The dispersive element may include a reflective diffraction grating configured to reflect and divide the incident light into the plurality of lights having the different output angles.

The reflective diffraction grating may be formed on a reflection plane which is inclined with respect to a light incident surface of the filter array.

The incident light may include a Raman scattered light, and the spectroscopy apparatus may further include a rejection filter configured to remove a component, other than the Raman scattered light, from the incident light to output a filtered light, and transfer the filtered light to the filter array.

The incident light may include a Raman scattered light, and the spectroscopy apparatus may further include a parabolic concentrator configured to collimate the incident light to the reflective diffraction grating.

The reflective diffraction grating may be formed on a curved reflection surface which is concavely curved toward a light incident surface of the filter array.

The spectroscopy apparatus may further include a focal lens configured to focus the plurality of lights output from the dispersive element, and transfer the focused plurality of lights to the filter array.

The dispersive element may include an interference filter.

The filter array may include filters which are concentrically arranged according to passbands of wavelengths of the filters.

The filter array, including transmissive filters or reflective filters, may be integrated into the detector according to passbands of wavelengths of the transmissive filters or reflective filters.

According to an aspect of another exemplary embodiment, there is provided a spectroscopy method, including: primarily dividing an incident light into a plurality of lights having different output angles; and secondarily dividing the plurality of lights, with a higher spectral resolution than a spectral resolution of the primary dividing.

The spectroscopy method may further include collimating the incident light before the primary dividing.

The primary dividing may include primarily dividing the incident light by a transmissive diffraction grating or a prism.

The primary dividing may include primarily dividing the incident light by a reflective diffraction grating.

The primary dividing may include primarily dividing the incident light by an interference filter.

The second dividing may include secondarily dividing the primarily divided light by filters which are concentrically arranged according to passbands of wavelengths of the filters.

The spectroscopy method may further include focusing the primarily divided light before the secondary dividing.

According to an aspect of another exemplary embodiment, there is provided a bio-signal measuring apparatus, including: a light source configured to emit a light onto an object; a spectroscopy apparatus configured to primarily divide the light which is incident onto the spectroscopy apparatus after being Raman scattered from the object, and secondarily divide the light with a higher spectral resolution than a spectral resolution of the primary divided light; and a detector configured to detect the light which has been secondarily divided by the spectroscopy apparatus.

The spectroscopy apparatus may include: a dispersive element configured to primarily divide the light incident from the object, with the spectral resolution of the primary dividing; and a filter array configured to secondarily divide the light, which has been divided by the dispersive element, with the higher spectral resolution than the spectral resolution of the primarily divided light.

The dispersive element may include a reflective diffraction grating which is formed on a reflection plane which is inclined with respect to a light incident surface of the of the filter array.

The incident light may include a Raman scattered light, and the spectroscopy apparatus further comprises a rejection filter configured to remove a component, other than the Raman scattered light, from the incident light to output a filtered light, and transfer the filtered light to the filter array.

The bio-signal measuring apparatus may further include a parabolic concentrator configured to collimate the incident light to the reflective diffraction grating.

The light emitted from the light source may be a monochromatic light or an infrared light.

BRIEF DESCRIPTION OF THE DRAWINGS

The above and/or other aspects will be more apparent by describing certain exemplary embodiments, with reference to the accompanying drawings, in which.

Figure 1A:
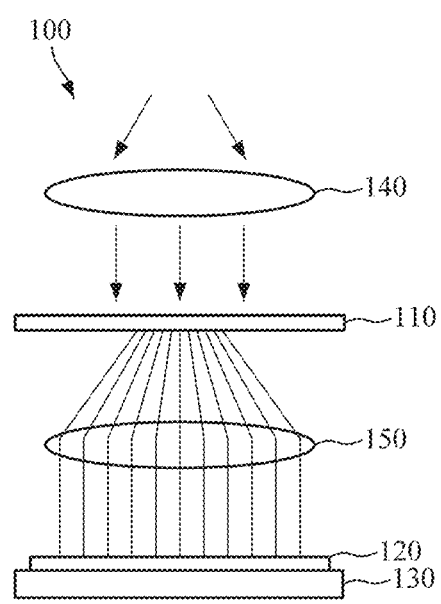
FIG. 1A illustrates a spectroscopy apparatus according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise.

In addition, unless explicitly described to the contrary, an expression such as "comprising" or "including" will be understood to imply the inclusion of stated elements but not the exclusion of any other elements. Also, the terms, such as 'part', 'unit' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list.

Figure 1B:
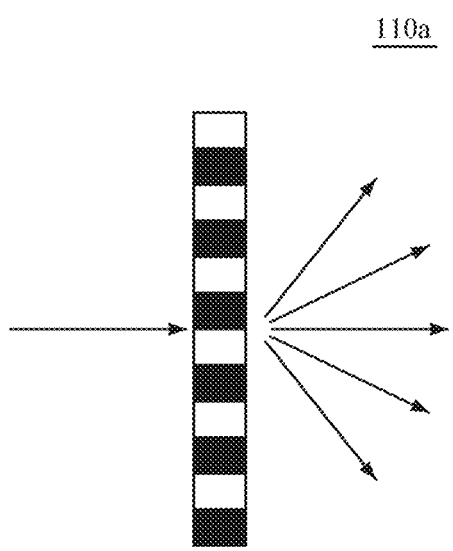
FIG. 1B illustrates a transmissive diffraction grating according to an exemplary embodiment.
Figure 2:
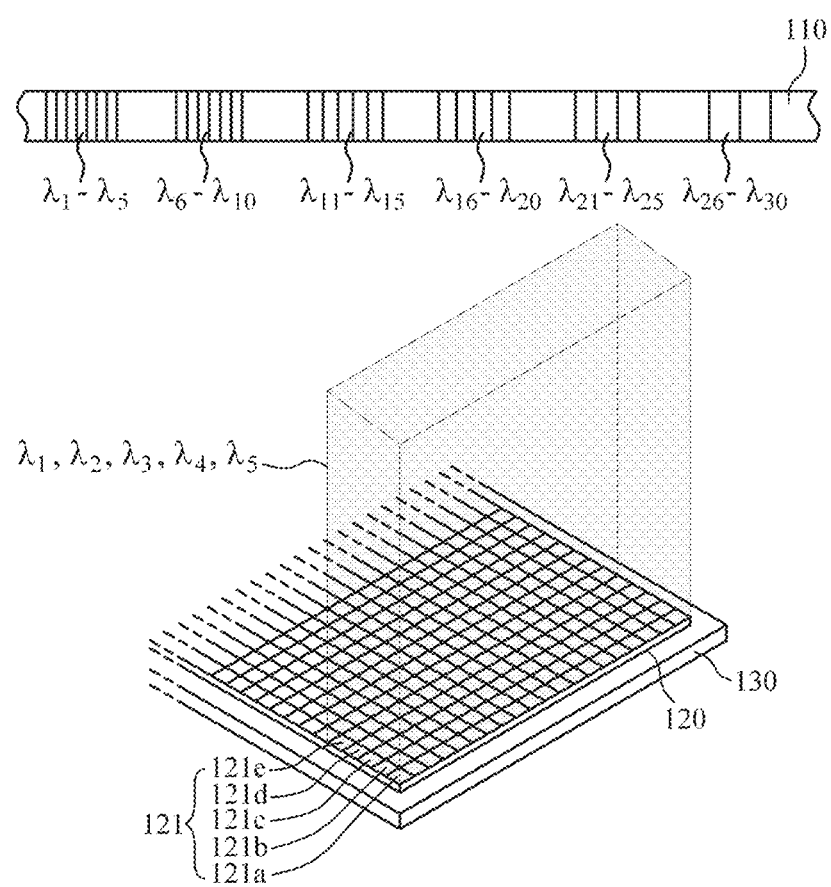
FIG. 2 illustrates an example of secondarily dividing light, which has been primarily divided, by filters shown in FIG. 1A.
Figure 3:
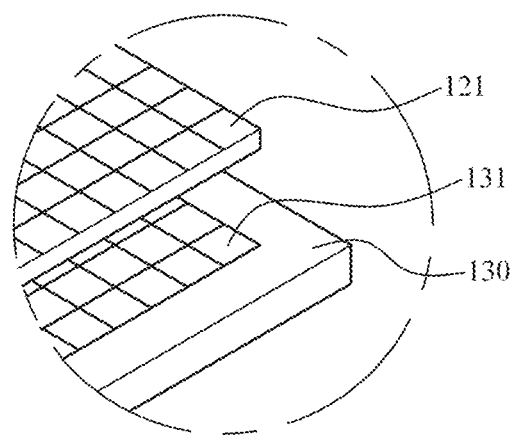
FIG. 3 is a partial exploded perspective view of a filter array according to an exemplary embodiment.
Figure 4:
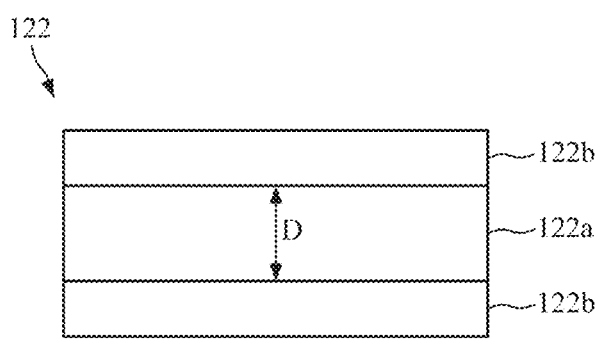
FIG. 4 is a cross-sectional view of a filter according to an exemplary embodiment.
Figure 5:
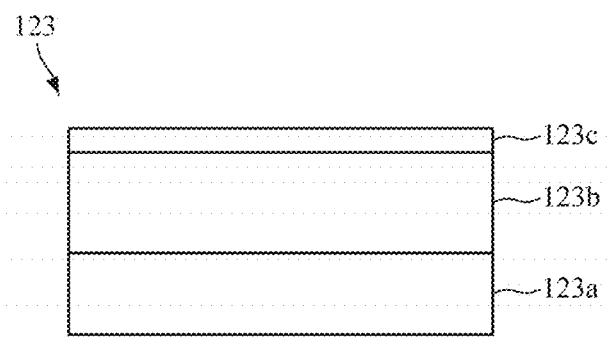
FIG. 5 is a cross-sectional view of a filter according to another exemplary embodiment.

FIG. 1A illustrates a spectroscopy apparatus according to an exemplary embodiment. FIG. 1B illustrates a transmissive diffraction grating according to an exemplary embodiment. FIG. 2 illustrates an example of secondarily dividing light, which has been primarily divided, by filters shown in FIG. 1A. FIG. 3 is a partial exploded perspective view of a filter array according to an exemplary embodiment. FIG. 4 is a cross-sectional view of a filter according to an exemplary embodiment. FIG. 5 is a cross-sectional view of a filter according to another exemplary embodiment.

With reference to FIGS. 1A to 5, a spectroscopy apparatus 100 may include a dispersive element 110, a filter array 120, a detector 130, a collimating lens 140, and a focal lens 150.

The dispersive element 110 primarily divides or splits an incident light. In particular, the dispersive element 110 divides the incident light into a plurality of beams travelling in different directions, according to wavelengths of the incident light, or devices/splits the incident light to have different output angles. Further, the dispersive element 110 arranges the divided incident light according to the wavelengths of the incident light. The filter array 120 secondarily divides light, which has been primarily divided by the dispersive element 110, with a higher spectral resolution than that of the dispersive element 110, and provides the divided light to the detector 130. That is, the filter array 120 may subdivide the light, which has been divided by the dispersive element 11 according to wavelengths of the light, and may provide the subdivided light to the detector 130.

The detector 130 is located at a focal length from the dispersive element 110 to realize the spectroscopy apparatus 100 in a small size. The focal length may refer to a distance from the dispersive element 110 to the detector 130. For example, the distance may be set to have a short focal length of 35 mm or less. Accordingly even when a spectral resolution of the dispersive element 110 is reduced, the spectroscopy apparatus 100 may maintain a high resolution with a small device size because the filter array 120 may provide a higher spectral resolution than the spectral resolution of the dispersive element 110 and may occupy a relatively small space. Thus, while maintaining a small size, the spectroscopy apparatus 100 may measure an incident light at a high resolution. Further, since the incident light is split by the dispersive element 110 to have different directions according to the wavelengths of the incident light, and then travels to respective spectral regions of the filter array 120, even when the spectral resolution of the filter array 120 is increased, light loss may be reduced as compared to a case where no dispersive element 110 is provided.

In the exemplary embodiment, the dispersive element 110 may include a diffraction grating that divides and diffracts a spectrum of light according to wavelengths. The diffraction grating may arrange light components in order of wavelength. The diffraction grating may be a transmissive diffraction grating 110a which splits and transmits a collimated incident light as shown in FIG. 1B.

The collimating lens 140 may be disposed front f the dispersive element 110 so that the light passes through the collimating lens 140 before reaching the dispersive element 110. The collimating lens 140 may collimate the incident light, and may transfer the collimated light to the transmissive diffraction grating. That is, the collimating lens 140 transforms the incident light into a parallel light, and transfers the parallel light to the dispersive element 110. The collimating lens 140 may be formed as a simple spherical lens or an aspherical lens.

For example, the dispersive element 110 may be implemented as a transmissive diffraction grating including a plurality of slits arranged at equidistant intervals. In the case where the transmissive diffraction grating is formed with a plurality of slits, the following operation may be performed.

The light incident onto the transmissive diffraction grating is diffracted and dispersed cylindrically according to Huygens' principle. If an optical path difference between rays passing through adjacent slits is equal to an integer multiple of the wavelength of the incident light, constructive interference occurs and an output light becomes brighter. However, if the optical path difference is not equal to any integer multiple of the wavelength, the output light becomes extinct. The condition that constructive interference occurs may vary depending on light wavelengths, such that a light having different wavelengths may be divided according to wavelengths by the transmissive diffraction grating.

The incident light is divided by the dispersive element 110, and then passes through the focal lens 150 to be transferred to the filter array 120. The focal lens 150 focuses the light onto a filtering surface of the filter array 120. The focal lens 150 may be a short focal length lens having a focal length of 35 mm or less, thereby further enabling a small size of the spectroscopy apparatus 100.

The filter array 120 may include filters 121 and may be integrated into the detector 130 according to wavelength ranges. In the case where the components of the light that has passed through the transmissive diffraction grating, are arranged in order of wavelength, and are transferred to the filter array 120, the filters 121 may be arranged in the same wavelength order of the components of light separated by the transmissive diffraction grating. The filters 121 may be arranged in a line according to wavelength ranges. The filters 121 may be arranged in a plurality of lines, each line having the same wavelength range.

The filters 121 may subdivide the light, which has been divided by the transmissive diffraction grating, into narrower beams according to the wavelengths of the light. For example, the filters 121 may receive with a light having a spectral resolution of 10 nm, and may divide the light to have a spectral resolution of 2 nm. For example, as shown in FIG. 2, the filter array 120 may include filters 121a, 121b, 121c, 121d, and 121e, which receive a light having wavelengths $\lambda_1, \lambda_2, \lambda_3, \lambda_4,$ and $\lambda_5$ in a range of 860 run to 870 nm. The filters 121a, 121b, 121c, 121d, and 121e may divide the received light into a spectrum having a spectral resolution of 2 nm. In this case, the filters 121a, 121b, 121c, 121d, and 121e may divide the received light, having wavelengths in a range of 860 nm to 870 nm, into a wavelength of 860 nm to 862 nm ($\lambda_1$), a wavelength of 862 nm to 864 nm ($\lambda_2$), a wavelength of 864 nm to 866 nm ($\lambda_3$), a wavelength of 866 nm to 868 nm ($\lambda_4$), and a wavelength of 868 nm to 870 nm ($\lambda_5$).

The filters 121 may receive other wavelengths of the light which is divided by the transmissive diffraction grating with a spectral resolution of 10 nm, and may also divide the received light with a spectral resolution of 2 nm as described in the above example. However, the spectral resolution is not limited thereto, and the filters 121 may divide light with spectral resolution higher or lower than the spectral resolution of 2 nm.

For example, the filters 121 may be transmissive filters. Each of the transmissive filters is adapted to transmit a light of a specific wavelength range. The transmissive filter may be a transmissive interference filter 122. As illustrated in FIG. 4, the transmissive interference filter 122 may be formed with semi-transparent reflective films 122b being attached to both sides of a transparent film 122a.

The transmissive interference filter 122 may selectively transmit light of a specific wavelength range, and may block the light of the other wavelengths. The transmission wavelength range of the transmissive interference filter 122 may depend on an optical thickness of the transmissive interference filter 122, which is be obtained by multiplying a refractive index by a thickness D of the transparent film 122a. The optical thickness of the transparent film 122a may be set to a half of a wavelength to be transmitted. The transmissive interference filters 122 may be arranged on the detector 130 with the optical thickness of the transparent film 122a being set differently for each wavelength. The transmissive interference filters 122 may have a high refractive thin film and a low refractive thin film which are alternately arranged.

In another example, the filter array 120, which includes reflective filters, may be integrated into the detector according to wavelength ranges. The reflective filter may be a reflective interference filter 123. As illustrated in FIG. 5, the reflective interference filter 123 may be formed with a transparent film 123b and a metallic semi-transparent film 123c being layered on a metallic mirror 123a. The reflective interference filter 123 may reflect only light of a specific wavelength range, and may transmit light of the other wavelengths, according to an optical thickness of the transparent film 123b.

The detector 130 may detect light, which is divided into wavelength ranges by the filter array 120, and may convert the detected light into an electric signal. The detector 130 may be an array of elements of any one type of photodiode, Charge Coupled Device (CCD), Complementary Metal-Oxide Semiconductor (CMOS), and the like, and may form detector pixels 131. For example, the filters 121 may be formed to correspond one-on-one to the detector pixels 131. In another example, one filer 121 may be formed to correspond to a plurality of adjacent detector pixels 131.

The detector pixels 131 may detect light which has passed through the respective filters 121. Also, the detector pixels 131 may convert the detected light into an electric signal, and may provide the electric signal to a signal processor. The signal processor processes the electric signal provided by the detector pixels 131. The signal processor may identify data addresses, at which the detector pixels 131 corresponding to the filters 121 are located, based on position data of the filters 121 for each wavelength range, may assign an identification number to the data addresses, and may generate address maps by matching the identification numbers with position numbers of the filters 121. The address maps may be stored in a memory.

The signal processor may obtain a quantity of light, which has passed through each of the filters 121, by using the address maps stored in the memory. In the case where the filter 121 is a transmissive filter, the signal processor may obtain the quantity of light, which has passed through each of the filters 121, as a light quantity for each wavelength. In the case where the filter 121 is a reflective filter, the signal processor may obtain a quantity of light by calculating a quantity of light reflected from each of the filters 121, based on the quantity of light which has passed through each of the filters 121.

For example, the quantity of light for each wavelength may be obtained by calculating a quantity of light reflected from each of the filters 121, based on the quantity of light which has passed through each of the filters 121, and by using simultaneous equations $\lambda_2+\lambda_3+\lambda_4+ \ldots \lambda_N=Q_1$, $\lambda_1+\lambda_3+\lambda_4+ \ldots \lambda_N=Q_2, \ldots$, and $\lambda_1+\lambda_2+\lambda_3 \ldots \lambda_{N-1}=Q_N$, in which $\lambda$ denotes a wavelength, and Q denotes a quantity of light.

Figure 6:
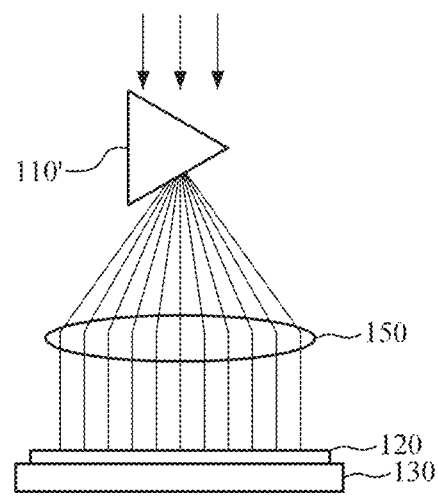
FIG. 6 illustrates a dispersive element according to an exemplary embodiment.

In another example, as illustrated in FIG. 6, a dispersive element 110' may include a prism. The prism may divide an incident light, which is collimated by a collimating lens 140, to have different output angles according to the wavelengths of the incident light, and may arrange the divided light. The prism is a transparent body having two or more optical surfaces capable of refracting light, with at least a pair of surfaces being formed in a non-parallel shape. The prism may be formed in a deltoid shape. When light passes through the prism, the light is dispersed since a refractive index varies depending on wavelengths, such that a spectrum may be obtained.

Light, divided by the prism, may pass through a focal lens 150 to be transferred to the filter array 120. The light divided by the prism may be focused on a filtering surface of the filter array 120 by the focal lens 150. The focal lens 150 is a short focal length lens which may further enable a small size of the spectroscopy apparatus 100, but is not limited thereto. The focal lens 150 may have a focal length of 35 mm or less.

As described above, the filter array 120 including the filters 121 may be integrated into the detector 130 according to wavelength ranges. In the case where the components of the light that has passed through the prism are arranged in order of wavelength, and are transferred to the filter array 120, the filters 121 may be arranged in the same order as the wavelength order of the components of light divided by the prism. The filters 121 may be arranged in a line according to wavelength ranges. The filters 121 may be arranged in a plurality of lines, each line having the same wavelength range. The filters 121 may subdivide the light, divided by the prism, into narrower beams according to wavelengths. The filter 121 may be a transmissive filter or a reflective filter.

As described above, the spectrometer apparatus 100 may include a transmissive diffraction grating or the prism as the dispersive element 110'; the detector 130 is located at a relatively short focal length from the dispersive elements 110 and 110' to enable a small size of the detector 130; and the filter array 120, which divides light to have a higher spectral resolution than that of the dispersive elements 110 and 110', is integrated into the detector 130. Accordingly, while maintaining a small size, the spectrometer apparatus 100 may measure an incident light at a high resolution, and light loss may be minimized.

A spectroscopy method performed by the spectroscopy apparatus 100 according to the exemplary embodiment may be described as follows.

The spectroscopy apparatus 100 may primarily divide an incident light. In this case, the transmissive diffraction grating of the dispersive element 110 or the prism of the dispersive element 110' may primarily divide the incident light. Accordingly, after passing through the dispersive elements 110 and 110', the incident light may be divided and arranged according to wavelengths. Before primarily dividing the incident light, the collimating lens 140 may collimate the incident light.

In the case of using an infrared spectroscopy method for measuring a bio-signal, the incident light may include light which is emitted onto an object, and is reflected therefrom. In the case of using Raman spectroscopy for measuring a bio-signal, the incident light may include light, which is obtained after monochromatic light is emitted onto an object and is Raman scattered therefrom. The object may be a living body such as human skin or an animal.

Then, the spectroscopy apparatus 100 may secondarily divide the light, which has been primarily divided, to have a higher spectral resolution than that of the primarily divided light. In this case, the primarily divided light may be secondarily divided by the filter array 120. The filter array 120 may subdivide the light, which has been primarily divided by the dispersive elements 110 and 110', into narrower beams.

Before secondarily dividing the light, the primarily divided light may be focused by the focal lens 150. Accordingly, the primarily divided light may be focused on a filtering surface of the filter array 120 by the focal lens 150, and may be secondarily divided by the filter array 120 to be provided to the detector 130. The detector 130 may detect the light, divided according to wavelengths by the filter array 120, and may convert the detected light into an electric signal. The signal processor may receive the electric signal from the detector 130 and may obtain the quantity of light for each wavelength.

Figure 7A:
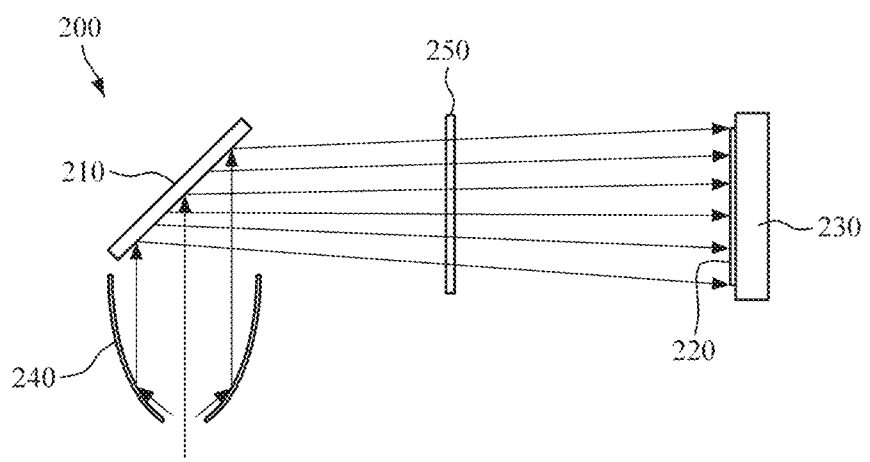
FIG. 7A illustrates a spectroscopy apparatus according to another embodiment.
Figure 7B:
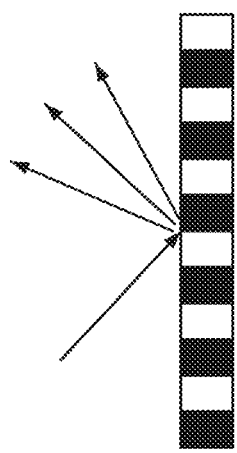
FIG. 7B illustrates a reflective diffraction grating according to an exemplary embodiment.

FIG. 7A is a diagram illustrating a spectroscopy apparatus according to another exemplary embodiment. FIG. 7B illustrates a reflective diffraction grating.

Referring to FIG. 7A, a spectroscopy apparatus 200 may include a dispersive element 210 and a filter array 220.

The dispersive element 210 includes a reflective diffraction grating 210a which reflects light while dividing the light as shown in FIG. 7B. The reflective diffraction grating 210a is formed on a reflection plane which is inclined with respect to a light incident surface. That is, the reflective diffraction grating 210a may include a plurality of grooves formed in parallel to each other at equidistant intervals, such that a spectrum may be obtained by the interference of diffracted light in each groove. Accordingly, the reflective diffraction grating 210a may divide the incident light at different angles according to wavelengths, and may reflect the divided light to the filter array 220.

In the case where the incident light includes light, which is obtained after monochromatic light is emitted onto an object and is Raman scattered therefrom, a parabolic concentrator 240 may collimate the incident light, including the Raman scattered light, to the reflective diffraction grating 210a. An apex portion of the parabolic concentrator 240 is disposed toward the object, and may have a hole for entry of the incident light. The parabolic concentrator 240 has a reflective inner surface, and an open portion which is disposed toward the reflective diffraction grating 210a, such that when the incident light enters into the parabolic concentrator 240 and is reflected from the reflective inner surface, the incident light may be collimated to the reflective diffraction grating 210a.

Further, a rejection filter 250 may remove components, other than Raman scattered light, from the incident light including Raman scattered light, and may transfer the light to the filter array 220. For example, in the case where a laser beam is emitted onto the object and is Raman-scattered therefrom, the laser beam is mixed with the Raman scattered light, and passes through the reflective diffraction grating 210a to proceed to the filter array 220. In this case, the rejection filter 250 may block the laser beam between the reflective diffraction grating 210a and the filter array 220, so that a laser beam having a high intensity may not be introduced into the filter array 220. The rejection filter 250 is adapted to remove a laser wavelength.

The filter array 220, including the above-described filters 121, may be integrated into the detector 230 according to wavelength ranges. The detector 230 may also be configured in substantially the same manner as the detector 130 described in the above example. In the case where the components of light are arranged in order of wavelength through the reflective diffraction grating 210a, and are transferred to the filter array 120, the filters 121 may be arranged in the same order as the wavelength order of the components of light divided by the reflective diffraction grating 210a. The filters 121 may be arranged in a line according to wavelength ranges. The filters 121 may be arranged in a plurality of lines, each line having the same wavelength range. The filters 121 may subdivide the light, divided by the reflective diffraction grating 210a, into smaller parts than the reflective diffraction grating 210a according to wavelengths. The filter 121 may be a transmissive filter or a reflective filter.

As described above, the spectrometer apparatus 200 according to the present exemplary embodiment includes a reflective diffraction grating 210a as the dispersive element 210 to disperse the incident light at different output angles according to the wavelengths of the incident light; the detector 230 is located at a relatively short focal length from the dispersive elements 210 to enable a small size of the spectrometer apparatus 200; and the filter array 220, which divides light to have a higher spectral resolution than that of the dispersive element 210, is integrated into the detector 230. Accordingly, while maintaining a small size, the spectrometer apparatus 200 may measure incident light at a high resolution, and light loss may be minimized.

A spectroscopy method performed by the spectroscopy apparatus 200 according to the exemplary embodiment may be described as follows.

The spectroscopy apparatus 200 may primarily divide an incident light by using the reflective diffraction grating of the dispersive element 210. In this case, while passing through the dispersive element 210, the incident light may be divided and arranged according to wavelengths. Before primarily dividing the incident light, the collimating lens 240 may collimate the incident light to the dispersive element 210.

Then, the spectroscopy apparatus 200 may secondarily divide the light, which has been primarily divided, to have a higher spectral resolution than the primarily divided light. In this case, the primarily divided light may be secondarily divided by the filter array 220. The filter array 220 may subdivide the light, which has been primarily divided by the dispersive element 210, into narrower beams.

In the case of using Raman spectroscopy for measuring a bio-signal, the spectroscopy apparatus 200 may remove a laser beam, other than Raman scattered light, from the primarily divided light by using the rejection filter 250 before secondarily dividing the light. The Raman scattered light, from which the laser beam is removed, may be secondarily divided by the filter array 220 and may be provided to the detector 230. The detector 230 may detect the light, which is divided according to wavelengths by the filter array 220, and may convert the detected light into an electric signal. The signal processor may receive the electric signal from the detector 230 and may obtain the quantity of light for each wavelength.

Figure 8:
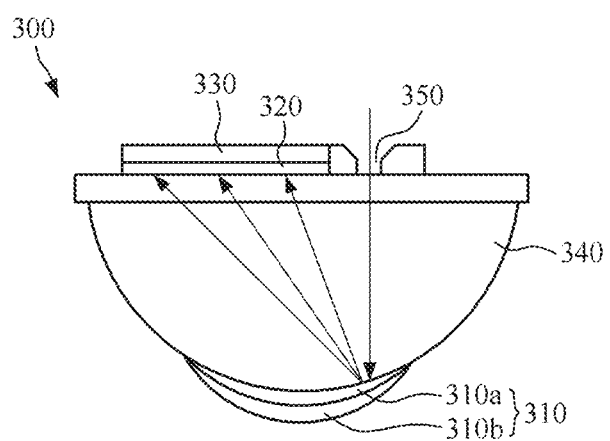
FIG. 8 illustrates a spectroscopy apparatus according to another exemplary embodiment.

FIG. 8 is a block diagram of a spectroscopy apparatus according to another exemplary embodiment.

Referring to FIG. 8, a spectroscopy apparatus 300 includes a dispersive element 310 and a filter array 320.

The dispersive element 310 includes a reflective diffraction grating formed on a curved reflection surface which is concavely curved toward a light incident surface of the filter array 320. The reflective diffraction grating may be formed with a plurality of grooves formed in parallel to each other at equidistant intervals, such that a spectrum may be obtained by the interference of diffracted light in each groove. Accordingly, the reflective diffraction grating may divide the incident light into a plurality of beams travelling in different directions, according to the wavelengths of the incident light, and may reflect the divided light to the filter array 320.

For example, the reflective diffraction grating may be formed on an outer surface of a lens 340. The lens 340 may be formed in a semi-spherical shape. The reflective diffraction grating may be disposed at the apex of the lens 340. The lens 340 may include a light-transmitting material. The lens 340 transfers light, which is incident through the slit 350, to the reflective diffraction grating, and focuses the light onto the filter array 320.

The reflective diffraction grating may include a diffraction layer 310a, which is formed on the outer surface of the lens 340, and a reflection layer 311b which is formed on an outer surface of the diffraction layer 310a. The diffraction layer 310a may have a plurality of grating grooves formed by nano imprinting and the like. The reflection layer 310b may include aluminum, gold, and the like.

The filter array 320, including the above-described filters 121, may be integrated into the detector 330 according to wavelengths. The detector 330 may be configured in substantially the same manner as the above-described detector 130. In the case where the components of the light that has passed through the reflective diffraction grating are arranged in order of wavelength, and are transferred to the filter array 320, the filters 121 may be arranged in the same order as the wavelength order of the components of light divided by the reflective diffraction grating. The filters 121 may be arranged in a line according to wavelength ranges. The filters 121 may be arranged in a plurality of lines, each line having the same wavelength range. The filters 121 may subdivide the light, divided by the reflective diffraction grating, into narrower beams than the reflective diffraction grating according to wavelengths. The filter 121 may be a transmissive filter or a reflective filter.

As described above, the spectrometer apparatus 300 according to the present embodiment may include a reflective diffraction grating as the dispersive element 310 to disperse the incident light at different output angles according to wavelengths; the detector 330 is located at a relatively short focal length from the dispersive element 310 to enable a small size of the spectrometer apparatus 300; and the filter array 320, which divides light to have a higher spectral resolution than that of the dispersive element 310, is integrated into the detector 330. Accordingly, while maintaining a small size, the spectrometer apparatus 300 may measure an incident light at a high resolution, and light loss may be minimized.

A spectroscopy method performed by the spectroscopy apparatus 300 according to the exemplary embodiment may be described as follows.

The spectroscopy apparatus 300 may primarily divide an incident light by using the reflective diffraction grating of the dispersive element 310. In this case, the incident light is incident into the dispersive element 310 through the slit 350, and after passing through the dispersive element 310, the incident light may be divided and arranged according to wavelengths. In this case, the lens 340 may transfer the light, which is incident through the slit 350, to the dispersive element 310, and may focus the light, which is divided by the dispersive element 310, onto the filter array 320.

Then, the spectroscopy apparatus 300 may secondarily divide the light, which has been primarily divided, to have a higher spectral resolution than that of the primarily divided light. The filter array 320 may subdivide the light, which has been primarily divided by the dispersive element 310, into narrower beams. The detector 330 may detect the light divided by the filter array 320 according to wavelengths, and may convert the detected light into an electric signal. The signal processor may receive the electric signal from the detector 330 and may obtain the quantity of light for each wavelength.

Figure 9:
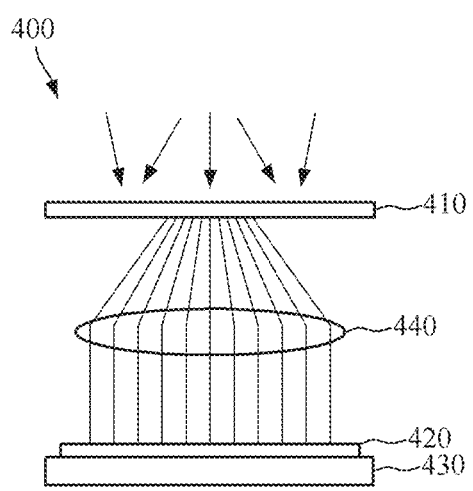
FIG. 9 illustrates a spectroscopy apparatus according to another exemplary embodiment.
Figure 10:
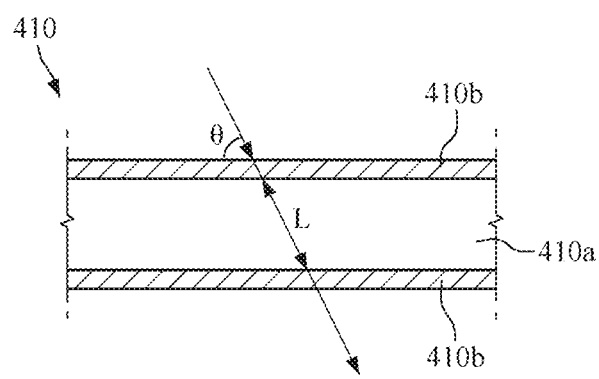
FIG. 10 is a cross-sectional view of an interference filter according to an exemplary embodiment.
Figure 11:
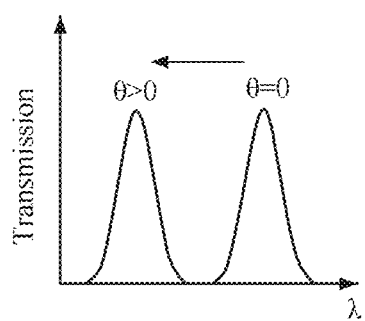
FIG. 11 is a graph explaining an operation of the interference filter illustrated in FIG. 10.
Figure 12:
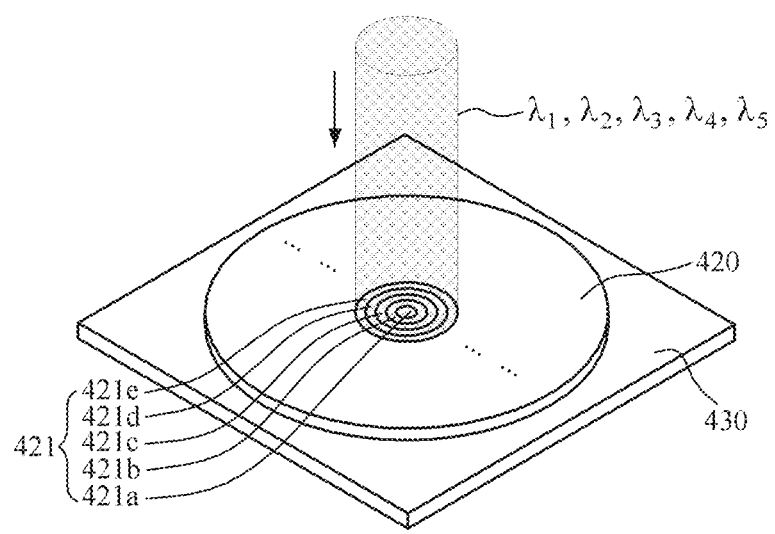
FIG. 12 illustrates an example of arrangement of filters according to wavelength ranges in accordance with FIG. 9.

FIG. 9 is a diagram illustrating a spectroscopy apparatus according to another exemplary embodiment. FIG. 10 is a cross-sectional view of an example of an interference filter according to an exemplary embodiment. FIG. 11 is a graph explaining an operation of the interference filter illustrated in FIG. 10. FIG. 12 illustrates an example of arrangement of filters according to wavelength ranges in accordance with FIG. 9.

Referring to FIGS. 9 to 12, the spectroscopy apparatus 400 includes a dispersive element 410 and a filter array 420.

The dispersive element 410 may include an interference filter. Once incident light is incident as diffused light, the interference filter concentrically divides and arranges the diffused light. For example, the interference filter may include semi-transparent reflective films 410$b$ disposed at a regular interval with a cavity 410$a$ therebetween.

The optical path length of light passing through the cavity 410$a$ may vary depending on angles of the diffused light incident into the interference filter. The optical path length may be obtained by multiplying a length of a path that light propagates through a medium by a refractive index of the medium. The optical path length of the diffused light passing through the cavity 410$a$ corresponds to a value obtained by multiplying a length of a path of the diffused light passing through the cavity 410$a$ by a refractive index of the cavity 410$a$.

As illustrated in FIGS. 10 and 11, among the diffused light incident into the interference filter, if light is incident at an angle at which the optical path length of the incident light is half the wavelength, the light is transmitted through the interference filter. Accordingly, the interference filter may concentrically divide and arrange the diffused light according to wavelengths. The interference filter may include a transparent film instead of the cavity 410$a$.

The light, divided by the interference filter, may pass through a focal lens 440 to be transferred to a filter array 420. The light, divided after passing through the interference filter, may be focused on a filtering surface of the filter array 420 by the focal lens 440. The focal lens 440 may be a short focal length lens having a focal length of 35 mm or less, thereby further enabling a small size of the spectroscopy apparatus 400. In addition, the focal lens 440 may be formed in various shapes as long as the focal lens 440 may perform the above function.

The filter array 420 may include filters 421 which are concentrically arranged according to wavelength ranges (e.g., according to a passband of wavelengths). Here, the filters 421 may be concentrically arranged according to wavelength ranges in the same order as the wavelength order of the components of light divided by the interference filter.

The filters 421 may be formed to correspond one-on-one to detector pixels of a detector 430. The detector pixels of the detector 430 may be configured in the same manner as the detector pixels 131 of the detector 130 described in the above example. In another example, one filter 421 may be formed to correspond to a plurality of adjacent detector pixels. The filters 421 may subdivide the light, divided by the interference filter, into smaller parts than the interference filter according to wavelengths. The filters 421 may be a transmissive filter or a reflective filter, and may be integrated into the detector 430.

For example, the filters 421 may receive light, divided by the interference filter with a spectral resolution of 10 nm, and may divide the light with a spectral resolution of 2 nm. In the case where the filters 421$a$, 421$b$, 421$c$, 421$d$, and 421$e$, among the filters 421 of the filter array 420, receive light having wavelengths $\lambda_1$, $\lambda_2$, $\lambda_3$, $\lambda_4$, and $\lambda_5$ in a range of 860 nm to 870 nm after the light is divided by the interference filter, the filters 421$a$, 421 $b$, 421$c$, 421$d$, and 421$e$ may divide the received light into a wavelength $\lambda_1$ of 860 nm to 862 nm, a wavelength $\lambda_2$ of 862 nm to 864 nm, a wavelength $\lambda_3$ of 864 nm to 866 nm, a wavelength $\lambda_4$ of 866 nm to 868 nm, and a wavelength $\lambda_5$ of 868 nm to 870 nm.

The filters 421, which receive light having other wavelengths after the light is divided by the interference filter with a spectral resolution of 10 nm, may also divide the received light with a spectral resolution of 2 nm as described in the above example. However, the spectral resolution is not limited thereto, and the filters 421 may divide light with spectral resolution higher or lower than the spectral resolution of 2 nm.

As described above, the spectrometer apparatus 400 according to the fourth exemplary embodiment includes the interference filter of the dispersive element 410 to disperse the incident light at different angles according to wavelengths; the detector 430 is located at a relatively short focal length (e.g., 35 mm or less) from the dispersive element 410 to enable a small size of the spectrometer apparatus 400; and the filter array 420, which divides light with a higher spectral resolution than that of the dispersive element 410, is integrated into the detector 430. Accordingly, while maintaining a small size, the spectrometer apparatus 400 may measure incident light with high resolution, and light loss may be minimized.

A spectroscopy method performed by the spectroscopy apparatus 400 according to the fourth exemplary embodiment may be described as follows.

The spectroscopy apparatus 400 may primarily divide incident light by using the interference filter of the dispersive element 410. In particular, the light is incident as diffused light into the dispersive element 410, and while passing through the dispersive element 410, the incident light may be concentrically divided and arranged according to wavelengths.

Then, the spectroscopy apparatus 400 may secondarily divide the light, which has been primarily divided, by using the filter array 420 with a higher spectral resolution than that of the primary dividing. In particular, the spectroscopy apparatus 400 may secondarily divide the light, which has been primarily divided, by using the filters 421 concentrically arranged according to wavelengths. The filters 421 may subdivide the light, which has been primarily divided by the dispersive element 410, into smaller parts than the primary dividing according to wavelengths.

Before secondarily dividing the light, the focal lens 440 may focus the primarily divided light. Accordingly, the primarily divided light may be focused on a filtering surface of the filter array 420 by the focal lens 440, and may be secondarily divided by the filter array 420 to be provided to the detector 430. The detector 430 may detect the light divided according to wavelengths by the filter array 420, and may convert the detected light into an electric signal. The signal processor may receive the electric signal from the detector 430 and may obtain the quantity of light for each wavelength.

Figure 13:
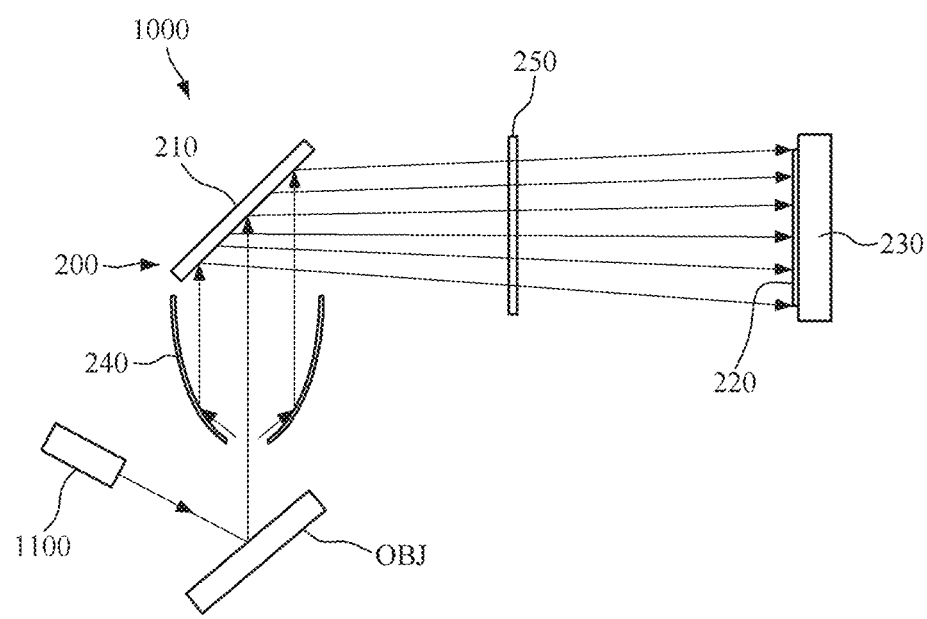
FIG. 13 illustrates a bio-signal measuring apparatus according to an exemplary embodiment.
Figure 14:
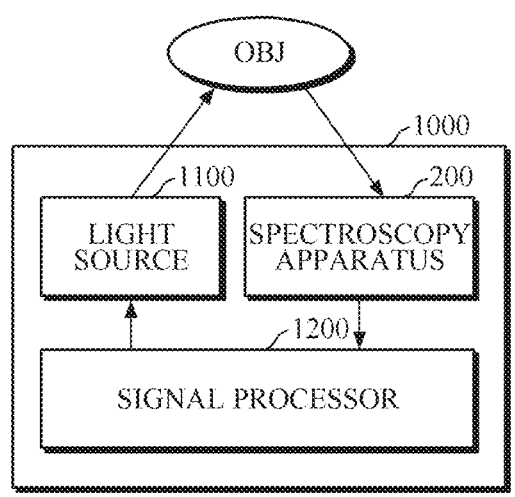
FIG. 14 is a control block diagram corresponding to the bio-signal measuring apparatus illustrated in FIG. 13.

FIG. 13 is a diagram illustrating a bio-signal measuring apparatus according to a first exemplary embodiment. FIG. 14 is a control block diagram illustrating an example of the bio-signal measuring apparatus illustrated in FIG. 13.

Referring to FIGS. 13 and 14, the bio-signal measuring apparatus 1000 according to the first exemplary embodiment includes a light source 1100 which emits monochromatic light onto an object OBJ and generates Raman scattering.

The light source 110 may include a laser light source which output a monochromatic laser beam. Light emitted by the light source 1100 may be directed to a required position of the object OBJ by at least one optical element. The light source 1100 may emit light onto the object OBJ according to a control signal of a signal processor 1200.

The light source 1100 may measure a bio-signal by using Raman spectroscopy. The Raman spectroscopy is a method of analyzing a biological signal (e.g., a blood glucose level) by emitting a laser beam onto an object, and by obtaining Raman shift by analyzing a wavelength of light radiating from the object.

Specifically, the Raman spectroscopy uses scattering of light, particularly inelastic scattering, which is generated after the light is incident into the object and collides with atoms or molecules in the object. Such scattering is generated not merely by light reflecting from the surface of atoms or molecules, but by light radiating after being absorbed into the atoms or molecules, and the scattered light has a wavelength that is longer than the wavelength of the incident light. A wavelength difference between the scattered light and the incident light may be approximately equal to or less than 200 nm. By analyzing a spectrum of the scattered light, various physical properties, such as molecular vibration and structure of molecules in the object, and the like, may be identified.

The bio-signal measuring apparatus 1000 may include any one of the spectroscopy apparatuses 100, 200, 300, and 400 according to the above-described first to fourth exemplary embodiments. The spectroscopy apparatuses 100, 200, 300, and 400 may primarily divide light, which is incident after being Raman-scattered from the object OBJ, and then may secondarily divide the light with a higher spectral resolution than that of the primary dividing.

For example, in the case where the bio-signal measuring apparatus 1000 includes the spectroscopy apparatus 200 according to the second exemplary embodiment, the dispersive element 210 includes a reflective diffraction grating which reflects the incident light while dividing the light. The reflective diffraction grating is disposed to be inclined or tilted with respect to a light incident surface of the filter array 220. The reflective diffraction grating may divide the incident light at different angles according to wavelengths and may reflect the divided light to the filter array 220. The parabolic concentrator 240 may collimate the incident light, including Raman-scattered light, to the reflective diffraction grating. Further, the rejection filter 250 may block a laser beam, other than the Raman scattered light, from the incident light including the Raman scattered light, and may transfer the light to the filter array 220.

The filter array 220 may secondarily divide the light, which has been divided by the reflective diffraction grating, with a higher spectral resolution than that of the reflective diffraction grating, and may provide the secondarily divided light to the detector 230.

The detector 230 may detect the light secondarily divided by the filter array 220. The detector 230 may detect the light divided by the filter array 220 into wavelengths, may convert the detected light into an electric signal, and may provide the electric signal to the signal processor 1200.

The signal processor 1200 may reconstruct a Raman spectrum by using a Raman light signal received from the detector 230, may differentiate between in vivo components by analyzing the reconstructed Raman spectrum, and may obtain information about concentration of each component and the like. For example, the in vivo components may include blood glucose, triglyceride, cholesterol, calories, protein, uric acid, and the like, but is not limited thereto.

Figure 15:
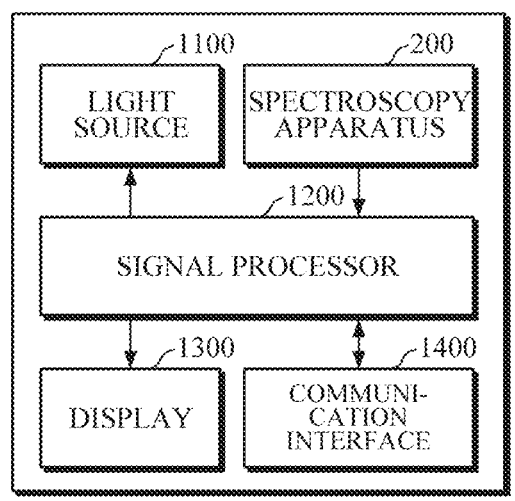
FIG. 15 is another control block diagram corresponding to the bio-signal measuring apparatus illustrated in FIG. 13.

As illustrated in FIG. 15, the bio-signal measuring apparatus 100 may further include a display 1300 and a communication interface 1400. The display 1300 and the communication interface 1400 may be mounted in the bio-signal measuring apparatus 1000.

The display 1300 may output various types of information under the control of the signal processor 1200. In this case, the display 1300 may display bio-signal information measured by the signal processor 1200, health state information related to the bio-signal information, warning or alarm information, and the like, and may display the information in various visual display methods to a user.

The display 1300 may include a touch module capable of touch input. In this case, the display 1300 may output a user interface, through which the display 1300 may receive a command input from a user, and may transmit the received command to the signal processor 1200. In addition, the bio-signal measuring apparatus 100 may include a separate manipulator for receiving a control command from a user and transmitting the received command to the signal processor 1200. The manipulator may include a power button and the like for inputting a command of turning on/off the power of the bio-signal measuring apparatus 1000.

The communication interface 1400 may be connected to a communication network by using a communication technique according to a control signal of the signal processor 1200, and may be connected to an external device, which is also connected to the same communication network, to transmit and receive necessary data. The signal processor 1200 may control the communication interface 1400 to be connected with the external device, and may process various operations in conjunction with the connected external device. In this case, the signal processor 1200 may provide necessary bio-signal information and the like to the external device according to a degree of bio-signal processing capability of the connected external device.

The communication technique may include Bluetooth communication, Bluetooth Low Energy (BLE) communication, Near Field Communication (NFC), WLAN (WIFI)

communication, Zigbee communication, Infrared Data Association (IrDA) communication, Wi-Fi Direct (WFD) communication, Ultra-Wideband (UWB) communication, Ant+ communication, WIFI communication, 3G communication, 4G communication, 5G communication, and the like but is not limited thereto.

For example, the communication interface 1400 may be connected with the external device through communications, and may transmit information, such as a measured bio-signal and the like, to the external device. Further, the communication interface 1400 may receive reference information, such as a reference blood glucose value and the like, for calibration of a bio-signal measuring apparatus from the external device, and may transmit the received reference information to the signal processor 1200.

In this case, the external device may be a smartphone, a smart pad, a desktop computer, a laptop computer, and other information processing devices, and may be a device which has a relatively higher computing performance than the bio-signal measuring apparatus 1000. However, the external device is not limited thereto.

In this manner, the bio-signal measuring apparatus 1000 may be manufactured in a small size and may measure bio-signals; and the external device may manage various types of information using the measured bio-signals, for example, statistical information including a bio-signal measurement history of a user, health state analysis based on the measurement history, change history information, and the like, and may provide the information in various manners, such as a graph and the like.

Figure 16:
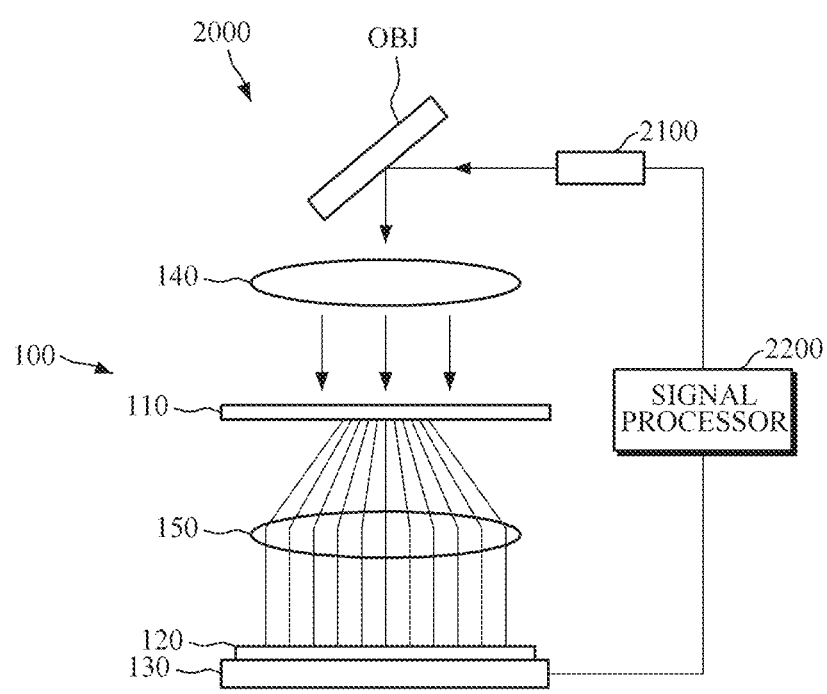
FIG. 16 illustrates a bio-signal measuring apparatus according to another exemplary embodiment.

FIG. 16 is a diagram illustrating a bio-signal measuring apparatus according to a second embodiment.

Referring to FIG. 16, the bio-signal measuring apparatus 2000 according to the second embodiment includes a light source 2100 which emits infrared light onto an object OBJ. The light source 2100 may be a light emitting diode (LED) or a halogen lamp which emits infrared light. Light emitted by the light source 2100 may be directed to a required position of the object OBJ by at least one optical element. The light source 2100 may emit light onto the object OBJ according to a control signal of a signal processor 1200.

The light source 2100 may enable measurement of a bio-signal by infrared spectroscopy. The infrared spectroscopy is a method of predicting a blood glucose level by emitting infrared light onto an object, by analyzing light radiating from the skin by diffused reflection, and by calculating a quantity of light absorbed by the blood glucose molecules in the skin. The infrared spectroscopy may use near infrared spectroscopy in a wavelength range of 750 nm to 2000 nm and mid infrared spectroscopy in a wavelength range of 2500 nm to 10000 nm.

The bio-signal measuring apparatus 2000 may include any one of the spectroscopy apparatuses 100, 300, and 400 according to the above-described first, third, and fourth embodiments. The spectroscopy apparatuses 100, 300, and 400 may primarily divide light which is incident after being reflected from the object.

For example, in the case where the bio-signal measuring apparatus 2000 includes the spectroscopy apparatus 100 according to the first embodiment, the dispersive elements 110 and 110' may be a transmissive diffraction grating or a prism which transmits the light while dividing the incident light collimated by the collimating lens 140. The light divided by the transmissive diffraction grating or the prism may pass through the focal lens 150 to be transferred to the filter array 120.

The filter array 120 may secondarily divide light, which has been divided by the transmissive diffraction grating or prism, with a higher spectral resolution than that of the trans-missive diffraction grating or prism, and may transfer the secondarily divide light to the detector 130.

The detector 130 may detect the light secondarily divided by the filter array 120. The detector 130 may detect the light, divided by the filter array 120 into wavelengths, may convert the detected light into an electric signal, and may provide the electric signal to the signal processor 2200.

The signal processor 2200 may reconstruct a Raman spectrum by using a signal received from the detector 130, may differentiate between in vivo components by analyzing the reconstructed infrared spectrum, and may obtain information about concentration of each component and the like. The bio-signal measuring apparatus 2000 according to this embodiment may further include the display 1300 and the communication interface 1400 of the bio-signal measuring apparatus 2000 according to the above-described embodiment.

In addition, the bio-signal measuring apparatuses 1000 and 2000 may be embedded in a wearable device, a mobile device such as a smartphone, a tablet PC, a laptop computer, and the like, a terminal such as a desktop computer, medical equipment, and the like. Further, the bio-signal measuring apparatuses 1000 and 2000 may be modified in various forms, such as an independent hardware device, and the like. Such bio-signal measuring apparatuses 1000 and 2000 may be used in the healthcare field by measuring various bio-signals in a non-invasive manner. Particularly, when embedded in a wearable device, a mobile device, and the like, the bio-signal measuring apparatuses 1000 and 2000 may be used in the mobile healthcare field.

For example, the bio-signal measuring apparatuses 1000 and 2000 may be manufactured in the form of a wearable device which has a main body and a strap to be worn on an object. Here, the wearable device may be a watch-type wearable device, a bracelet-type wearable device, wristband-type wearable device, a ring-type wearable device, a glasses-type wearable device, a hairband-type wearable device, and the like, but the shape and size are not limited thereto.

The light sources 1100 and 2100, the spectroscopy apparatuses 100, 200, 300, and 400, and the signal processors 1200 and 2200 may be mounted in the main body of the bio-signal measuring apparatuses 1000 and 2000. When the bio-signal measuring apparatuses 1000 and 2000 are manufactured as a watch-type wearable device, the light sources 1100 and 2100, the spectroscopy apparatuses 100, 200, 300, and 400 may be mounted at the bottom of the main body which contacts a wrist of a user; and the signal processors 1200 and 2200 may be mounted in an internal substrate of the main body to be electrically connected with the bio-signal measuring apparatuses 1000 and 2000 and the spectroscopy apparatuses 100, 200, 300, and 400. The strap may be made of a flexible material to bend around a user's wrist, and a battery for supplying power to the main body may be mounted in the strap if necessary.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A spectroscopy apparatus, comprising:
a dispersive element configured to divide an incident light into a plurality of lights having different output angles; and
a filter array comprising a plurality of filters which are concentrically arranged according to wavelength passbands of the plurality of filters, and configured to divide the plurality of lights to have different wavelengths, with a higher spectral resolution than a spectral resolution of the dispersive element, and provide the divided plurality of lights to a detector,
wherein the plurality of filters are arranged in a same wavelength order of the plurality of lights divided by the dispersive element, and are integrated into the detector.

2. The spectroscopy apparatus of claim 1, further comprising a collimating lens configured to collimate and transfer the incident light to the dispersive element.

3. The spectroscopy apparatus of claim 1, wherein the dispersive element comprises a transmissive diffraction grating configured to divide the incident light into the plurality of lights having the different output angles.

4. The spectroscopy apparatus of claim 1, wherein the dispersive element comprises a prism configured to divide the incident light into the plurality of lights having the different output angles.

5. The spectroscopy apparatus of claim 1, wherein the dispersive element comprises a reflective diffraction grating configured to reflect and divide the incident light into the plurality of lights having the different output angles.

6. The spectroscopy apparatus of claim 5, wherein the reflective diffraction grating is formed on a reflection plane which is inclined with respect to a light incident surface of the filter array.

7. The spectroscopy apparatus of claim 6, wherein the incident light comprises a Raman scattered light, and the spectroscopy apparatus further comprises a rejection filter configured to remove a component, other than the Raman scattered light, from the incident light to output a filtered light, and transfer the filtered light to the filter array.

8. The spectroscopy apparatus of claim 6, wherein the incident light comprises a Raman scattered light, and the spectroscopy apparatus further comprises a parabolic concentrator configured to collimate the incident light to the reflective diffraction grating.

9. The spectroscopy apparatus of claim 5, further comprising a lens,
wherein the reflective diffraction grating is formed on a curved reflection surface of the lens which is concavely curved to direct the plurality of lights toward a light incident surface of the filter array.

10. The spectroscopy apparatus of claim 1, further comprising a focal lens configured to focus the plurality of lights output from the dispersive element, and transfer the focused plurality of lights to the filter array.

11. The spectroscopy apparatus of claim 9, wherein the reflective diffraction grating is disposed at an apex on an outer surface of the lens, and
the spectroscopy apparatus further comprises a reflection layer disposed on an outer surface of the reflective diffraction grating.

12. The spectroscopy apparatus of claim 1, wherein the filter array, including transmissive filters or reflective filters, is integrated into the detector according to the wavelength passbands of the transmissive filters or reflective filters.

13. A spectroscopy method, comprising:
primarily dividing an incident light into a plurality of lights having different output angles; and
secondarily dividing the plurality of lights to have different wavelengths, with a higher spectral resolution than a spectral resolution of the primary dividing, by a plurality of filters which are concentrically arranged according to wavelength passbands of the plurality of filters and provide the secondarily divided plurality of lights to a detector,
wherein the plurality of filters are arranged in a same wavelength order of the plurality of lights divided by a dispersive element, and are integrated into the detector.

14. The spectroscopy method of claim 13, further comprising collimating the incident light before the primary dividing.

15. The spectroscopy method of claim 14, wherein the primary dividing comprises primarily dividing the incident light by a transmissive diffraction grating or a prism.

16. The spectroscopy method of claim 13, wherein the primary dividing comprises primarily dividing the incident light by a reflective diffraction grating.

17. The spectroscopy method of claim 13, wherein the primary dividing comprises primarily dividing the incident light by an interference filter.

18. The spectroscopy method of claim 13, further comprising focusing the primarily divided light before the secondary dividing.

19. A bio-signal measuring apparatus, comprising:
a light source configured to emit a light onto an object;
a spectroscopy apparatus comprising a dispersive element configured to primarily divide the light, which is incident onto the spectroscopy apparatus after being Raman scattered from the object, into a plurality of lights having different angles, and a plurality of filters which are concentrically arranged according to wavelength passbands of the plurality of filters, and configured to secondarily divide the plurality of lights to have different wavelengths with a higher spectral resolution than a spectral resolution of the dispersive element; and
a detector configured to detect the divided plurality of lights,
wherein the plurality of filters are arranged in a same wavelength order of the plurality of lights divided by the dispersive element, and are integrated into the detector.

20. The bio-signal measuring apparatus of claim 19, wherein the dispersive element comprises a reflective diffraction grating which is formed on a reflection plane which is inclined with respect to a light incident surface of the of the plurality of filters.

21. The bio-signal measuring apparatus of claim 20, wherein the incident light comprises a Raman scattered light, and the spectroscopy apparatus further comprises a rejection filter configured to remove a component, other than the Raman scattered light, from the incident light to output a filtered light, and transfer the filtered light to the plurality of filters.

22. The bio-signal measuring apparatus of claim 20, further comprising a parabolic concentrator configured to collimate the incident light to the reflective diffraction grating.

23. The bio-signal measuring apparatus of claim 19, wherein the light emitted from the light source is a monochromatic light or an infrared light.

\* \* \* \* \*